United States Patent [19]

Horwitz et al.

[11] Patent Number: 4,548,790
[45] Date of Patent: Oct. 22, 1985

[54] METHOD FOR EXTRACTING LANTHANIDES AND ACTINIDES FROM ACID SOLUTIONS

[75] Inventors: E. Philip Horwitz; Dale G. Kalina, both of Naperville; Louis Kaplan, Lombard; George W. Mason, Clarendon Hills, all of Ill.

[73] Assignee: The United States of America as represented by the United States Department of Energy, Washington, D.C.

[21] Appl. No.: 517,475

[22] Filed: Jul. 26, 1983

[51] Int. Cl.[4] .................... C01G 56/00; C01F 17/00; C01F 9/53; C07C 103/00
[52] U.S. Cl. ........................................ 423/9; 423/10; 423/21.5; 252/627; 252/631; 564/15
[58] Field of Search ................ 423/9, 10, 21.5, 8; 564/15; 252/631

[56] References Cited

U.S. PATENT DOCUMENTS 3,243,254 3/1966 Siddall .................................... 423/9
3,993,728 11/1976 Schulz .................................... 423/9
4,396,556 8/1983 Kem ................................ 423/10 X

OTHER PUBLICATIONS

Kalira, D. G. et al., "The Extraction of Am(III) and Fe(III) by Selected Dihexyl N,N–Dialkylcarbamoyl Methyl-Phosphonates, -Phosphinates and -Phosphine Oxides from Nitrate Media", *Separation Sci. and Tech.*, 16 (9), pp. 1127–1145, (1981).
Horwitz, E. P. et al., "Selected Alkyl(Phenyl)-N,-N-Dialkylcarbamoylmethylphosphine Oxides as Extractants for Am(III) from Nitric Acid Media", *Separation Sci. and Tech.*, 17 (10), pp. 1261–1279, (1982).
Medved, T. Ya. et al., "Dialkyl(Diaryl)[Dialkylcarbamoylmethyl] Phosphine Oxides", *Izv. Akad. Nauk SSSR*, Ser. Khim., 9, pp. 2121–2127, (1981), (Chem. Abst. 96: 35411, (1982)).
Matrosov, E. I. et al., "Protonation of Carbamoylmethyl-Phosphoryl Compounds", *Dokl. Akad. Nauk SSSR*, 273(6), pp. 1419–1422, [Phys. Chem.], (1983), (Chem. Abst. 100: 21005).
Chmutova, M. K. et al., "Extraction of Transplutonium Elements with Diphenyl(Alkyl)Dialkylcarbamoylmethylphosphine Oxides", *J. Radioanal. Chem.* 80 (1–2), pp. 63–69, (1983), (Chem. Abst. 99: 202203).
Horwitz, E. P. et al., "The Extraction of Th(IV) and U(VI) by Dihexyl-N,N-Diethylcarbamoylmethylphosphonate from Aqueous Nitrate Media", *Separation Sci. and Tech.*, 16(4), pp. 403–416, (1981).
Horwitz, E. P. et al., "The Extraction of Selected Transplutonium(III) and Lanthanide(III) Ions by Dihexyl-N,N-Diethylcarbamoylmethylphosphonate from Aqueous Media", *Separation Sci. and Tech.*, 16(4), pp. 417–437, (1981).
Muscatello et al., "The Extraction of Am(III) and Eu(III) from Aqueous Ammonium Thiocyanate by Dihexyl-N,N-Diethylcarbamoylmethylphosphonate and Related Compounds", *Separation Sci. and Tech.*, 16(6), p. 859, (1982).
Horwitz et al., "Carbamoylmethylphosphoryl Derivatives as Actinide Extractants and their Significance in the Processing and Recovery of Plutonium and other Actinides", *Plutonium Chemistry*, ACS Symp. Series, 216, Chapt. 22, p. 433 (1983), ed. by William T. Carhell and Gregory R. Choppin.

*Primary Examiner*—Teddy S. Gron
*Assistant Examiner*—Virginia B. Caress
*Attorney, Agent, or Firm*—James W. Weinberger; Walter L. Rees; Judson R. Hightower

[57] ABSTRACT

A process for the recovery of actinide and lanthanide values from aqueous acidic solutions with an organic extractant having the formula:

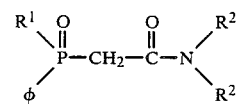

where $\phi$ is phenyl, $R^1$ is a straight or branched alkyl or alkoxyalkyl containing from 6 to 12 carbon atoms and $R^2$ is an alkyl containing from 3 to 6 carbon atoms. The process is suitable for the separation of actinide and lanthanide values from fission product values found together in high level nuclear reprocessing waste solutions.

15 Claims, 4 Drawing Figures

METHOD FOR EXTRACTING LANTHANIDES AND ACTINIDES FROM ACID SOLUTIONS

CONTRACTUAL ORIGIN OF THE INVENTION

The U.S. Government has rights in this invention pursuant to Contract No. W-31-109-ENG-38 between the U.S. Department of Energy and Argonne National Laboratory.

BACKGROUND OF THE INVENTION

This invention relates to a method for the recovering of lanthanide and actinide values from aqueous acid solutions. More specifically, the invention relates to a method for the recovering and separation of multivalent lanthanide and actinide values from aqueous acid waste solutions containing these and other values.

The disposition of the waste which results from the reprocessing of irradiated nuclear power reactor fuel elements is one of the major problems facing the nuclear power industry today. One approach is to solidify the liquid wastes as they come from the reprocessing facility into a stable solid material which can be stored in the earth for a period of time sufficient for the radiation to decay to safe levels. However, the storage times required to achieve safe levels of radioactivity are on the order of one million years. This is far longer than the geological stability of the earth can be expected to be maintained. One solution is to remove the extremely long-lived radioactive components, such as the actinides, i.e. the uranium, americium, cerium, plutonium and neptunium and the lanthanides, from the waste solution so that the remaining radioactive elements, representing the bulk of the radioactive waste, need only be stored for up to 1000 years before the radioactivity decays to background levels. This time period is within the realm of determining geological integrity. The lanthanides and actinides thus recovered from the waste can then be reprocessed and recycled to provide additional fuel for nuclear reactors and for isotopic power sources.

Another approach is to minimize the volume of radioactive waste by first removing the actinides, particularly plutonium and americium, and then removing the major heat producing isotopes $^{90}Sr$ and $^{137}Cs$. The remaining waste is not sufficiently radioactive to require placement in a deep geological repository. $^{90}Sr$ and $^{137}Cs$ have commercial applications. Only the actinide fraction would require placement in a deep geological repository. The volume of the TRU fraction (neptunium, plutonium, and americium) is approximately 1% of the total high level radioactive waste generated in a plutonium production plant.

The problem with recovering the lanthanides and actinides from large volumes of acidic high-level radioactive waste solutions is to find methods, using extractants, which will do so effectively and economically, since the lanthanides and actinides are present in several valence states and difficult to recover together.

One group of extractants which have been considered for the extraction of lanthanide and actinide values from aqueous acid waste solutions are the bidentate organophosphorous compounds. These compounds are described in U.S. Pat. No. 3,243,254 which issued Mar. 29, 1966 to Thomas Siddall III and is assigned to the common assignee. These extractants, include di-n-hexyl N,N-dibutyl carbamylmethylenephosphonate, di-n-octyl N,N-diethyl carbamylphosphonate, dibutyl N,N-diethyl carbamylphosphonate, and dihexyl N,N-diethyl carbamylmethylene phosphonate. These extractants have generally proven satisfactory although distribution ratios for some lanthanides and actinides are small, so that separation from other values found in the reprocessing solution is not always satisfactory. Furthermore, acid concentration ranges of the feed solutions is critical to extractability and the extractants are susceptible to radiolytic and hydrolytic damage which reduce their effectiveness.

SUMMARY OF THE INVENTION

A process has been developed for the extraction of multivalent lanthanide and actinide values from acidic waste solutions, and for the separation of these values from fission product and other values, which utilizes a new series of neutral bi-functional extractants, the alkyl(phenyl)-N,N-dialkylcarbamoylmethylphosphine oxides. These extractants have distribution ratios for lanthanides and actinides which are significantly improved over the prior art extractants, and because the alkoxy group is no longer present, the new series is more resistant to hydrolytic and radiolytic damage. The extractants are acid dependent, i.e. the extractability of the lanthanide and actinide values increases directly with increased acid concentration of the feed solution which simplifies recovery of the extracted values from the extractant. The extractant will recover trivalent and tetravalent lanthanide values and trivalent, tetravalent and hexavalent actinide values, so that valence adjustment in the feed solution is not necessary. The invention is a process for the recovery of multivalent lanthanide and actinide values from an aqueous acid solution containing these and other values by adjusting the concentration of the acid solution from 0.1 to 12.0M in acid to form a feed solution, contacting the feed solution with an extraction solution consisting of an extractant in a water-immiscible diluent, the extractant having the formula:

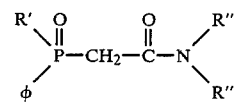

where $\phi$ is phenyl, R' is a straight or branched alkyl or alkoxyalkyl containing from 6 to 12 carbon atoms and R'' is an alkyl containing from 3 to 6 carbon atoms, whereby the multivalent lanthanide and actinide values are extracted by the extraction solution, separating the extraction solution from the feed solution, and stripping the lanthanide and actinide values from the extraction solution.

It is therefore one object of the invention to provide an improved process for recovery of multivalent lanthanide and actinide values from aqueous acid solutions.

It is another object of the invention to provide an improved process for recovering multivalent lanthanide and actinide values from aqueous acid solutions which utilizes an extractant having an improved distribution ratios for these values over prior art extractants.

Finally, it is the object of the invention to provide an improved process for the recovery and separation of multivalent lanthanide and actinide values from fission product and other values present together in a aqueous acid nuclear waste reprocessing solutions.

DETAILED DESCRIPTION OF THE PREFERRED EMBODIMENT

Figure 1:
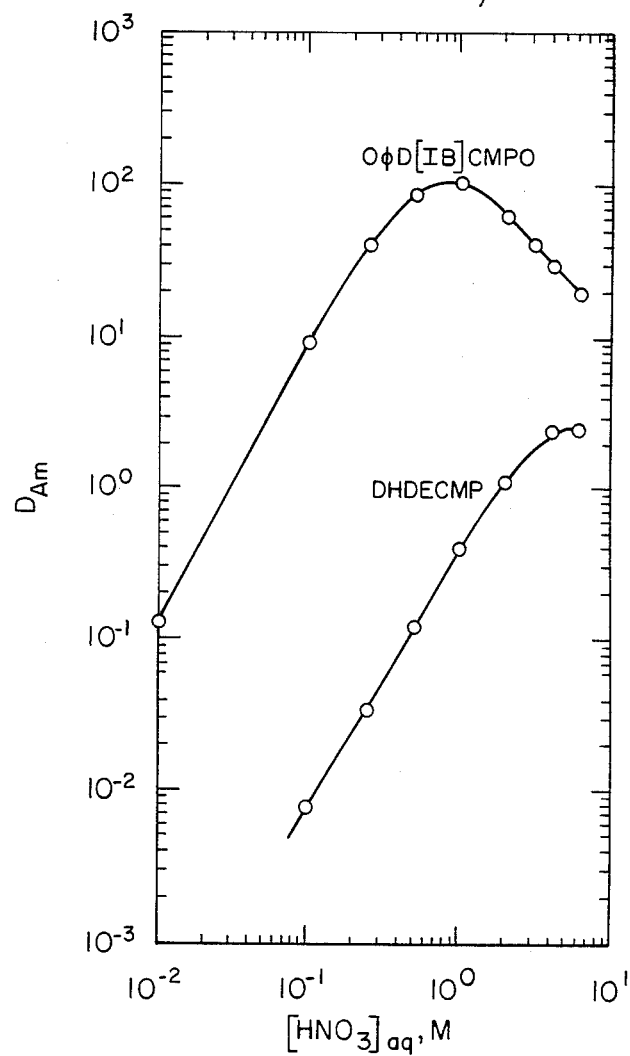
FIG. 1 is a graph comparing distribution ratios of americium to acid concentration, between an extractant of the invention and a prior art extractant.

These and other objects of the invention for recovering multivalent lanthanide and actinide values from a nitric acid nuclear fuel waste reprocessing solution containing these and fission product and other values may be met by adjusting the aqueous solution to between 0.5 and 5.0 molar nitric acid and adding about 0.075M oxalic acid to form a feed solution, contacting the feed solution with an extraction solution of 0.4M octyl(-phenyl)-N,N-diisobutylcarbamoylmethylphosphine oxide (hereinafter referred to as O$\phi$D[IB]CMPO) in diethylbenzene (DEB), to extract the multivalent lanthanide and actinide values from the aqueous feed solution, separating the loaded extraction solution from the aqueous phase, and contacting the loaded extraction solution with an aqueous solution which is about 0.05 to 0.1M in nitric acid to strip the lanthanide and actinide values from the extraction solution, thereby recovering the multivalent lanthanide and actinide values.

The process of the invention is useful for recovering lanthanide and actinide values from aqueous acid solution containing these and fission product and metal values such as iron and zirconium. Since the extractants will remove trivalent, tetravalent and hexavalent lanthanides and actinides equally well, no valence adjustment is necessary. The acid solution may be any strong mineral acid such as nitric, hydrochloric or perchloric acid. The acid concentration for the feed solution must be adjusted to between 0.1 and 10.0M preferably 0.2 and 5.0M for nitric acid and from 0.35 to 6M, preferably between 0.5 and 5.0M for perchloric and from 6–12M for hydrochloric acid in order for the values to extract. The feed solution may also be made from 0.05 to 0.2M, preferably about 0.075M, in oxalic acid. The oxalic acid complexes any iron, zirconium or molybdenum values which may be present in the waste solution to prevent them from being co-extracted with the lanthanide and actinide values.

This process is particularly suitable for the recovery of lanthanides and actinides from waste solutions resulting from fuel reprocessing by the Purex process which are generally from about 1.0 to 3.0M in nitric acid.

The extractant may be one of a series of several neutral bifunctional organophosphorous compounds containing a phenyl. Generally, the compounds are alkyl(-phenyl)-N,N-dialkylcarbamoylmethylphosphine oxides having the structural formula:

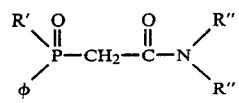

where R' is a straight or branched alkyl or alkoxyalkyl containing 6 to 12 carbon atoms and R" is an alkyl containing 3 to 6 carbon atoms.

The addition of the phenyl group was found to unexpectedly increase the bonding strength of the compound for lanthanides and actinides at high acidities and lower the bonding strength of the compound for the same group of elements at low acidities over similar prior art compounds which contained two alkyls on the phosphorous atom. This, however, resulted in a compound with limited solubility in diluents and which readily formed a second organic phase upon even a small amount of loading. An increase in the length of the amine alkyls to at least 3 carbon atoms, preferably to the isobutyl alkyl, restored most of the solubility and elminated the second phase formation. The phosphorous alkyl or alkoxyalkyl is preferably branched, such as a trimethyl pentyl alkyl. The extractants are prepared and purified as described in *Separation Science and Technology*, 17(10) pp. 1261–1279, 1982, incorporated herein by reference.

Concentration of the extractant in the extraction solution may vary from 0.1 to 0.5M, preferably 0.3 to 0.4M. By combining the extractant of the invention with a second phosphate extractant such as tri-n-butyl phosphate, (TBP), dibutylbutylphosphonate, (DBBP), or trialkylphosphine oxide, it is possible to further reduce the extractant concentration while retaining the same extraction capability. For example, 0.25M O$\phi$D[IB]CMPO and 0.75M TBP in decalin has about the same extraction power for actinides and lanthanides as 0.5M O$\phi$D[IB]CMPO has alone. Another example is a solution of 0.20M 2,4,4 trimethylpentyl-N,N-diisobutylcarbamoylmethylphosphine oxide and 1.2M tributylphosphate in kerosene. Non-phosphorous-based extractants which contain a basic donor group e.g. sulfoxide, amide or ketone may also be combined with the extractants of the invention. For example, an extraction solution of 0.25M O$\phi$D[IB]CMPO, 0.75M methylisobutyl ketone in decalin.

The diluent may be any inert, water-immiscible aromatic or aliphatic hydrocarbon such as diethylbenzene (DEB), diisopropylbenzene, xylene, decalin, dodecane or kerosine, or a chlorinated carbon such as carbon tetrachloride, or a hydrogen bonding diluent such as a water-immiscible carboxylic acid.

The loaded extracting solution, after contact with the feed solution, may be contacted with a 0.1 to 10.0M, preferably 0.5 to 5.0M nitric acid solution to scrub any fission product values which may have co-extracted with actinide and lanthanide values.

The actinide and lanthanide values may be recovered by contacting the loaded extractant with an aqueous acid solution which is less than 0.1M in acid to strip the extracted values from the extraction solution. Preferably the strip solution is from 0.01 to 0.05M in nitric acid.

The extraction temperature is not critical and may be carried out over a range from about 25° to 75° C. with 50° C. generally preferred due to the self-heating effect of the radioactive solutions. In general, contact times are not critical, although 30 seconds has been found satisfactory to ensure phase mixing. The actual extraction operation can be carried out in batch or continuous operations, using, for example, simple mixer-settlers, direct or countercurrent flow, centrifugal contactors, liquid-liquid extraction in a chromatographic column or using similar conventional type equipment known to those skilled in the art. Phase ratios can be varied depending upon engineering considerations and economic factors.

The following Examples are given to illustrate the process of the invention and are not to be taken as limiting the scope of the invention as defined by the appended claims.

EXAMPLE I

In order to compare the extractant of the invention with the prior art extractants of Siddall, extraction solutions of dihexyl-N,N-diethylcarbamoylmethylphosphonate (DHDECMP) dihexyl, N,N-diethylcarbamoylmethylphosphine oxide (DHDECMPO) and n-octyl(phenyl)-N,N-diisobutylcarbamoylmethylphosphine oxide (O$\phi$D[IB]CMPO) were prepared.

Extraction studies were performed using $^{230}$Th, $^{233}$U, $^{237}$Np, $^{239}$Pu, $^{242}$Pu, $^{241}$Am, and $^{243}$Cm. Standard radiometric assay and counting procedures were used throughout. Distribution ratios were determined at 25° C. For Np(IV) and Pu(IV) D's, extractions were performed from 3M HNO$_3$ containing 0.1M sulfamic acid-0.05M ferrous sulfamate, and 0.05M sodium nitrite, respectively. Multiple scrubs (usually 2 to 3) of the loaded organic phases were performed until two successive equilibrations gave the same distribution ratios. The distribution ratio for Np(V) was measured using a mixture of 237,239$_{Np}$ that was separated from Np(IV) and Np(VI) by cation ion exchange from 1M HNO$_3$. The distribution ratios of fission products were measured from synthetic HLLW using an Instruments SA, Inc. inductively coupled atomic emission spectrometer (argon plasma). Since only aqueous phases could be analyzed by ICP/AES, the metal ion constituents of the organic phases were quantitatively back-extracted by first diluting the equilibrated organic phase with 2-ethylhexanol (10% by volume) and then equilibrating the resultant mixture twice with an equal volume of an aqueous solution containing 0.01M NaCN, 0.05M diethylenetriaminepentaacetate (DTPA), and 0.50M NH$_4$OH. Distribution ratios measured by ICP/AES anaylsis were estimated to have a standard deviation of 20%.

Table I below shows a general comparison of three essential properties of a liquid-liquid extraction system; namely, distribution ratio, selectivity, and solubility of loaded organic phase, for the hexylethyl analogs of two prior art extractants and for O$\phi$D[IB]CMPO. The selectivity of AM(III) over Fe(III) is a good indication of selectivity of actinide (III) ions over a number of fission products whose reversible D's are more difficult to measure, e.g., Zr.

As the Table shows, the O$\phi$D[IB]CMPO compensates, to a large degree, for the unfavorable properties of the DHDECMPO.

TABLE I

| Comparisons of 0.5 M Solutions of Extractants in DEB. 3 M HNO$_3$, 25° C. | | | | |
|---|---|---|---|---|
| | | Am | % Loading | |
| Extractant | D$_{Am}$ | Fe | Nd(III)* | U(VI)* |
| DHDECMP | 1.8 | 3 × 10$^3$ | >75 | 100 |
| DHDECMPO | 22 | 4 × 10$^{-1}$ | 65–70 | 30–35 |
| O$\phi$D[IB]CMPO | 41 | 3 × 10$^3$ | >75 | 40–45 |

*Percent loadings are based on an extractant-to-metal ratio of 3 for Nd(III) and 2 for U(VI)

EXAMPLE II

FIG. 1 is a comparison between the acid dependencies of D$_{Am}$ using 0.5M DHDECMP, and O$\phi$[IB]CMPO solutions in DEB. Although all show a progressive increase in D$_{Am}$ with increasing acidity, the O$\phi$D[IB]CMPO shows a very high D$_{Am}$ over a range of acidity from 0.1M to 6M HNO$_3$ and probably much higher.

EXAMPLE III

Figure 2:
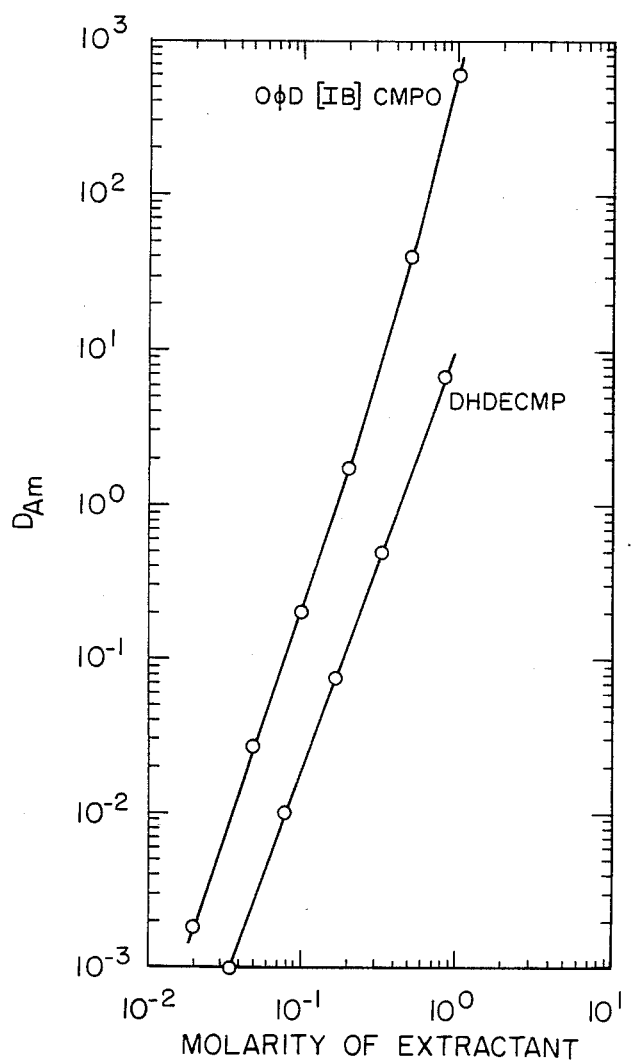
FIG. 2 is a graph comparing distribution ratio of americium to molarity between an extractant of the invention and a prior art extractant.

FIG. 2 shows the extractant dependency for D$_{Am}$ from 3M HNO$_3$ using the same two extractants as Example II. All two extractants show approximately third power dependencies although the CMPO compound shows a tendency toward higher dependencies above 0.5M. Because of the very strong extraction capability of O$\phi$D[IB]CMPO, a 0.5M concentration is sufficient whereas 0.8 to 1.0M is a useful concentration range for the phosphonate extractant.

EXAMPLE IV

A number of additional alkyl(phenyl)-N,N-dialkyl compounds of the invention were prepared in the manner described previously. These were 6-methylheptyl(-phenyl)-N,N-diisobutylcarbamoylmethylphosphine oxide (6-MH$\phi$D[IB]CMPO), and 2-ethylhexyl(phenyl)-N,N-diisobutylcarbamoylmethylphosphine oxide (2-EH$\phi$D[IB]CMPO).

Extractant solutions were prepared using distilled-in-glass grade o-xylene and diethylbenzene (DEB). Aqueous solutions were prepared using ultrapure water and ultrex grade nitric acid. Extraction studies were performed using $^{241}$Am, $^{152,154}$Eu, and $^{55}$Fe.

All distribution ratio mesurements were performed at 25° C. Duplicate assays of each phase were performed for both $^{55}$Fe and $^{241}$Am-$^{152,154}$Eu. Distribution ratios were reproducible within ±5%. In some distribution ratio measurements performed with HNO$_3$ solutions in the 10$^{-2}$ to 10$^{-1}$M range, the aqueous phase was made 10$^{-3}$M in Lu(NO$_3$)$_3$ to minimize the effect of acidic extractant impurities on D$_{Am}$ and D$_{Fe}$. This was found to be necessary with 6-MH$\phi$D[IB]CMPO for Am(III) and for all extractants with Fe(III).

The nitric acid extractions were performed by equilibrating a given organic phase four successive times with an equal volume of nitric acid solution. The nitric acid in the resultant organic phase was then back-extracted and titrated. Essentially quantitative extraction of Nd(III) and U(VI) was observed after each incremental addition of metal ion until either third phase formation occurred or 75% of saturation of the extractant was achieved.

Figure 3:
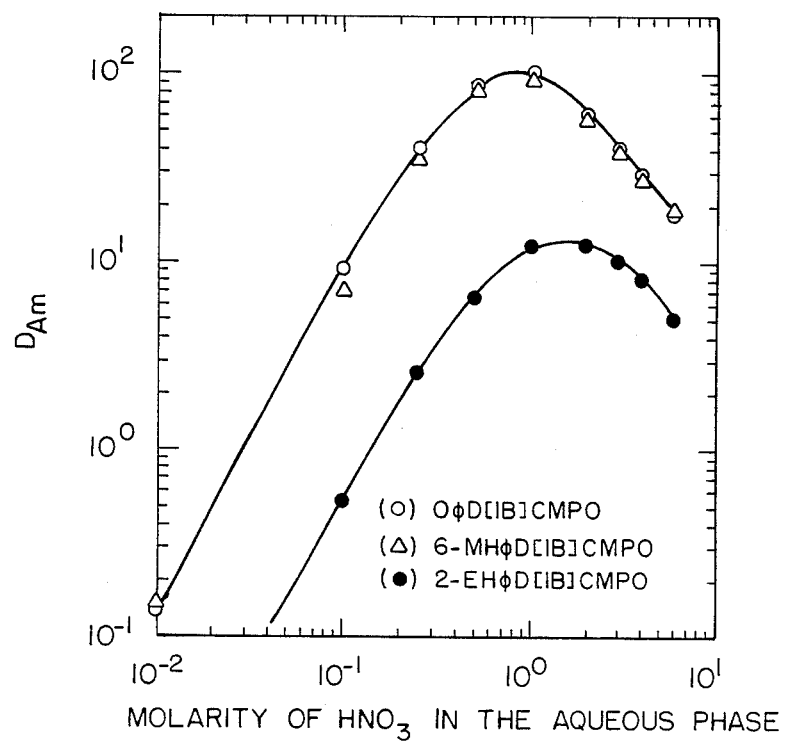
FIG. 3 is a graph comparing the distribution ratio of americium to molarity of acid for three extractants of the invention.

FIG. 3 shows a comparison of the D$_{Am}$ vs aqueous HNO$_3$ concentration for three octyl isomers of phenyl N,N-diisobutyl CMPO. No difference in D$_{Am}$ is observed between the n-octyl and 6-methylheptyl compounds since the branching of the octyl group is too far removed from the P=O group to influence bonding to Am(III). However, in the case of the 2-ethylhexyl isomer, a significant diminution in $D_{Am}$ is found. This is probably due to congestion around the metal center in the extracted complex which interferes with bonding. It is interesting to note that the decrease in $D_{Am}$ with 2-EH$\phi$D[IB]CMPO is less at high acidities, possibly because the 2-ethylhexyl compound bonds less readily to $HNO_3$.

Although the magnitude of $D_{Am}$ changes with the structural modifications described above, the general shape of the $D_{Am}$ vs $HNO_3$ curves is the same.

EXAMPLE V

Figure 4:
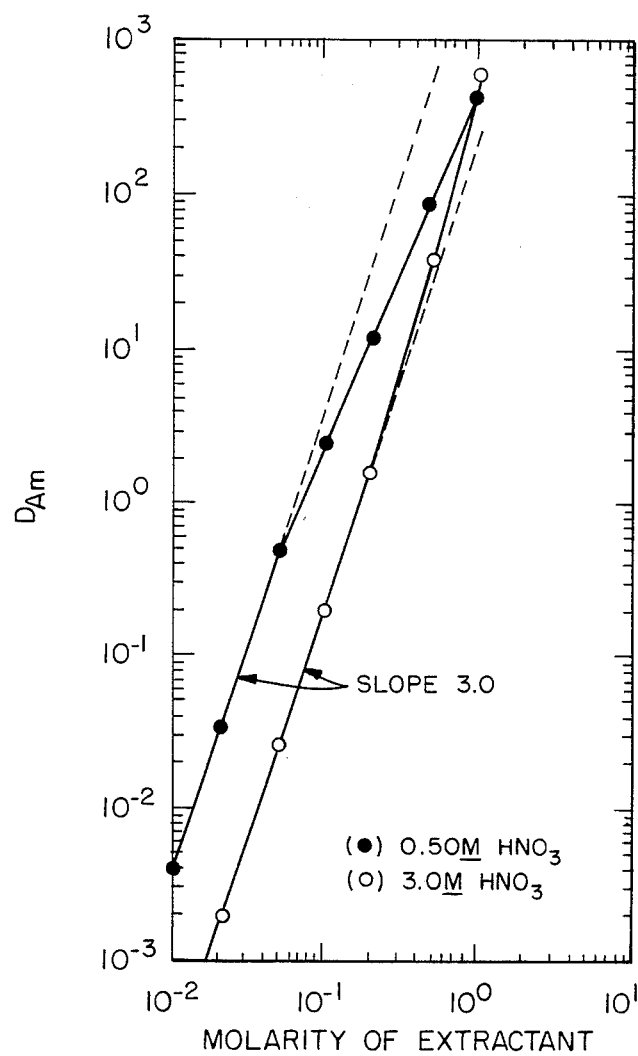
FIG. 4 is a graph comparing the distribution ratio of americium to molarity of O$\phi$D[IB]CMPO in DEB for two acid concentrations.

The variations in $D_{Am}$ as a function of extractant concentration for O$\phi$D[IB]CMPO is shown in FIG. 4. The extractant dependency was performed at low and high acidity. The extractant shows third-power dependencies at low concentrations for both acidities.

EXAMPLE VI

Table II shows the substantial improvement in selectivity of Am(III) over Fe(III) achieved with two alkyl(-phenyl)-N,N-dialkyl CMPO extractants compared to DHDECMPO. Although Fe(III) is only one of many constituents in high level radioactive waste, it was found that if a given extractant does not have very good selectivity for Am(III) over Fe(III), it will not have sufficiently high selectivity for Am(III) over important fission products such as Zr(IV), Nb(V), and Mo(VI). Note, the substantially higher $\alpha_{Fe}^{Am}$ values achieved with H$\phi$DECMPO and O$\phi$D[IB]CMPO.

TABLE II

Separation Factor $\alpha_{Fe}^{Am}$ as a Function of Nitric Acid Concentration[a] 0.5 M Extractant, 25° C.

| [HNO$_3$] | DHDECMPO | H$\phi$DECMPO | O$\phi$D[IB]CMPO |
|---|---|---|---|
| 0.50 | 6.1 | 2.8 × 10$^2$ | 1.1 × 10$^2$ |
| 1.0 | 5.2 | 2.4 × 10$^2$ | 1.4 × 10$^2$ |
| 2.0 | 1.8 | 1.0 × 10$^2$ | 7.6 × 10$^1$ |
| 4.0 | 1.0 × 10$^{-1}$ | 7.2 | 8.7 |
| 6.0 | 9.9 × 10$^{-3}$ | 0.60 | 1.2 |

[a]Separation factor, $\alpha_{Fe}^{Am} = D_{Am}/D_{Fe}$.

EXAMPLE VII

In Table III below are listed the distribution ratios for most of the fission products produced in spent fuel. Also included are corrosion products Cr, Fe, and Ni. The aqueous acidity and temperature were adjusted to correspond to conditions which would occur in the feed plus scrub processes. The D's for Am(III) and Cm(III) were included to evaluate selectivity. As can be seen from the data, Am(III) and Cm(III), which are the least extractable actinides [Pu(III) follows Am(III) closely], are selectively extracted from all of the fission products except lanthanides for each of the three extractants. The presence of oxalic acid is required to complex Zr(IV) and Mo(VI). The data for Tc indicates that poor decontamination from this fission product would be achieved. Also the D's for Pd and Ru are mixed distribution ratios. The fraction of Pd and Ru which extracts does not readily scrub out a loaded organic phase.

TABLE III

Distribution Ratios (Measured by ICP/AES) from Synthetic HLLW. 50° C.

| Element | 0.4 M O$\phi$D[IB]CMPO in DEB |
|---|---|
| Rb | <0.001 |
| Sr | 0.003 |
| Y | 1.7 |
| Zr | 0.19 |
| Mo | 0.66 |
| *Tc | 1.2 |
| Ru | 0.083 |
| Rh | 0.10 |
| Pd | 0.19 |
| Ag | <0.6 |
| Cd | 0.056 |
| *Cs | <0.001 |
| Ba | <0.007 |
| Cr | <0.09 |
| Fe | 0.08 |
| Ni | <0.2 |
| La | 2.4 |
| Ce | 3.4 |
| Pr | 4.5 |
| Nd | 5.6 |
| Pm | — |
| Sm | 9.1 |
| Eu | 8.0 |
| Gd | 1.9 |
| *Am | 9.4 |
| *Cm | 7.2 |

*Radiochemical Measurements

It can be seen from the preceding Examples and discussion that the process of the invention, for the recovery of multivalent actinide and lanthanide values from aqueous acid solutions and from fission product values, which utilizes the new series of neutral bifunctional extractants containing the phenyl group present a substantial improvement over the prior art extractants.

The embodiments of this invention in which an exclusive property or privilege is claimed are defined as follows:

1. A process for the recovery of multivalent lanthanide and actinide values from an aqueous acid solution containing these and other values comprising:
   adjusting the molarity of the acid in the aqueous solution to between 0.1 and 12.0M to form a feed solution;
   contacting the feed solution with an extraction solution consisting of an organic extractant in an inert water-immiscible organic diluent, the extractant having the formula:

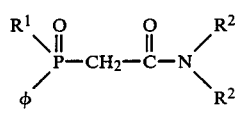

where $\phi$ is phenyl, R' is a straight or branched alkyl containing from 6 to 12 carbon atoms and R$^2$ is an alkyl containing from 3 to 6 carbon atoms, whereby the multivalent lanthanide and actinide values are selectively extracted from the feed solution, thereby loading the extraction solution,
   separating the loaded extraction solution from the feed solution, and
   stripping the lanthanide and actinide values from the extraction solution, thereby recovering the lanthanide and actinide values.

2. The process of claim 1 wherein the aqueous acid feed solution is a strong mineral acid selected from the group consisting of nitric, hydrochloric and perchloric acid.

3. The process of claim 2 wherein the feed solution also contains from 0.05 to 0.2M oxalic acid.

4. The process of claim 3 wherein the feed solution is from 0.1 to 10M in nitric acid.

5. The process of claim 4 wherein the feed solution is from 0.5 to 5.0M in nitric acid.

6. The process of claim 5 wherein the extraction solution is from 0.1 to 0.5M in organic extractant.

7. The process of claim 6 wherein the lanthanide and actinide values are recovered by contacting the loaded extraction solution with an aqueous solution that is about 0.05 to 0.1M in nitric acid to strip the lanthanide and actinide values from the loaded extraction solution.

8. The process of claim 7 wherein R' is selected from the group consisting of octyl, 2,4,4-trimethylpentyl, 6-methylheptyl and 2-ethylhexyl, and R² is isobutyl.

9. The process of claim 8 including the additional step of contacting the loaded extraction solution with a 0.1 to 10.0M nitric acid solution to scrub any fission product values from the solution which may be co-extracted with the lanthanide and actinide values.

10. The process of claim 9 wherein the water-immiscible organic diluent is an aromatic or aliphatic hydrocarbon selected from the group consisting of diethylbenzene, diisopropylbenzene, xylene, decalin, dodecane, and kerosine.

11. A process for recovering multivalent lanthanide and actinide values from a nitric acid nuclear fuel waste reprocessing solution containing these values together with fission product and other metal values comprising:
adjusting the molarity of the acid in the waste solution to between 0.5 and 5.0M and adding from 0.05 to 0.2M oxalic acid to the waste solution to form a feed solution:
contacting the feed solution with an extraction solution of 0.1 to 0.5M of an organic extractant having the formula:

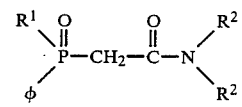

where $\phi$ is phenyl, R' is a straight or branched alkyl containing from 6 to 12 carbon atoms and R² is an alkyl containing from 3 to 6 carbon atoms in an inert water-immiscible aromatic or aliphatic hydrocarbon diluent, whereby the multivalent lanthanide and actinide values are selectively extracted from the feed solution thereby loading the extraction solution,
separating the loaded extraction solution from the feed solution, and
contacting the loaded feed solution with a 0.05 to 0.1M nitric acid solution to strip the lanthanide and actinide values from the extraction solution, thereby recovering the lanthanide and actinide values.

12. The process of claim 11 including the additional step of contacting the loaded extraction solution with a 0.1 to 10.0M nitric acid solution to scrub any fission product values from the solution which may be co-extracted with the lanthanide and actinide values.

13. A compound having the structural formula:

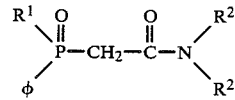

where $\phi$ is phenyl, $R^1$ is a straight or branched alkyl containing from 6 to 12 carbon atoms and $R^2$ is an alkyl containing from 3 to 6 carbon atoms.

14. The compound of claim 13 wherein $R^1$ and $R^2$ are branched.

15. The compound of claim 14 wherein $R^1$ is selected from the group consisting of octyl, 2,4,4-tri-methylpentyl, 6-methylheptyl and 2-ethylhexyl, and $R^2$ is isobutyl.

* * * * *